(12) United States Patent
Miller et al.

(10) Patent No.: US 10,238,116 B2
(45) Date of Patent: Mar. 26, 2019

(54) COMPOSITE LAUNDRY ADDITIVE

(71) Applicant: Dune Sciences, Inc., Eugene, OR (US)

(72) Inventors: John M. Miller, Eugene, OR (US); Richard T. Geiger, Eugene, OR (US)

(73) Assignee: Dune Sciences, Inc., Eugene, OR (US)

( * ) Notice: Subject to any disclaimer, the term of this patent is extended or adjusted under 35 U.S.C. 154(b) by 107 days.

(21) Appl. No.: 15/382,145

(22) Filed: Dec. 16, 2016

(65) Prior Publication Data

US 2018/0168163 A1   Jun. 21, 2018

(51) Int. Cl.

| | |
|---|---|
| C11D 17/06 | (2006.01) |
| A01N 59/16 | (2006.01) |
| A01N 25/08 | (2006.01) |
| C11D 3/48 | (2006.01) |
| D06M 11/83 | (2006.01) |
| C11D 3/00 | (2006.01) |
| C11D 3/40 | (2006.01) |
| C11D 7/20 | (2006.01) |
| C11D 11/00 | (2006.01) |
| C11D 17/00 | (2006.01) |
| C11D 17/04 | (2006.01) |

(52) U.S. Cl.
CPC ............. *A01N 59/16* (2013.01); *A01N 25/08* (2013.01); *C11D 3/0068* (2013.01); *C11D 3/40* (2013.01); *C11D 3/48* (2013.01); *C11D 7/20* (2013.01); *C11D 11/0017* (2013.01); *C11D 17/0039* (2013.01); *C11D 17/041* (2013.01); *D06M 11/83* (2013.01)

(58) Field of Classification Search
CPC ....... C11D 17/0039; C11D 3/505; C11D 3/40; C11D 17/06
USPC .......................................... 510/276
See application file for complete search history.

(56) References Cited

U.S. PATENT DOCUMENTS

| | | | |
|---|---|---|---|
| 2004/0067159 A1* | 4/2004 | Carnes ................... | A01N 25/04 422/28 |
| 2011/0224120 A1* | 9/2011 | Meine ...................... | C11D 1/04 510/337 |
| 2011/0294713 A1* | 12/2011 | Fernandes ............... | C09B 63/00 510/276 |
| 2012/0003289 A1* | 1/2012 | Sunder ................... | C11D 3/1206 424/404 |
| 2017/0275576 A1* | 9/2017 | Mort, III ................ | C11D 3/40 |
| 2017/0321171 A1* | 11/2017 | Heppert ............ | C11D 17/0039 |
| 2018/0015009 A1* | 1/2018 | Soubiran .................. | A61K 8/11 |

* cited by examiner

*Primary Examiner* — Gregory E Webb
(74) *Attorney, Agent, or Firm* — Schwabe, Williamson & Wyatt, P.C.

(57) ABSTRACT

A composite laundry additive made of composite particles. The composite particles comprising: a carrier component comprising one or more different inorganic support particles, wherein at least one of the inorganic support particles is a pigment particle; and a silver component comprising a silver metal or silver salt disposed on one or more of the inorganic support particles.

19 Claims, 6 Drawing Sheets

COMPOSITE LAUNDRY ADDITIVE

TECHNICAL FIELD

This disclosure is related to a new laundry additive and more specifically to a composition that delivers silver to the surface of textiles, for example using a wash-in or spray-on application.

BACKGROUND

Silver has been widely used as an antimicrobial agent for more than 2000 years to create clean drinking water and to prevent infections. The use of silver includes both metallic silver, such as for drinking vessels or tableware, and metal salts, including silver nitrate and silver chloride, that have been used in a wide variety of products ranging from the treatment of infections to the purification of swimming pools. In its ionic form, silver is unique because it attacks infection and odor-causing bacteria through multiple pathways. In addition, silver is immune to acquired antimicrobial resistance that plagues conventional antibiotics.

Recently, silver in the form of silver nanoparticles, silver-containing zeolites, silver salts, other silver-containing compounds, and polymers has found application in medical, consumer and industrial products to reduce the harmful effects of bacteria as well as to prevent odors and other effects from bacteria. The use of finely divided silver metal or weakly soluble silver salts enables efficient release of silver ions in the presence of moisture to provide active protection against undesirable effects of bacteria. The great majority of these active silver-based ingredients are incorporated into these products during the manufacturing process using a range of application methods including: 1) master-batch formulation of, e.g. polymer fibers that incorporate/embed the active ingredients; 2) ion exchange into zeolite particles that are then formulated into final products; or 3) topical coatings that are applied in a manufacturing system. While many of these products have proven to have beneficial properties, their antibacterial properties can wear out long before the textile wears out. In addition, there remains significant challenges related to discoloration of articles treated with silver metal particles (they are typically yellow in color due to plasmon absorption) or silver salts that can significantly darken due to photoreduction. Further, there are very few products available for application and/or reapplication of these benefits directly by consumers.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1:
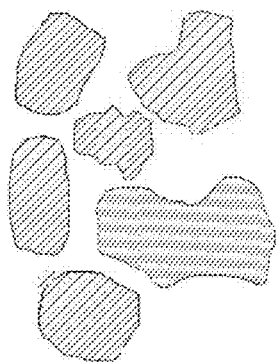
FIG. 1 is a schematic showing blue pigment particles with irregular shape and average size between 250-500 nm, in accordance with embodiments disclosed herein.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Disclosed herein are novel laundry additive compositions that deliver silver to the surface of textiles, for example using wash-in or spray-on applications. One of the primary benefits of the disclosed laundry additives is that they provide deodorizing and/or antimicrobial/antibacterial activity to a textile through the controlled release of silver ions. When incorporated into a laundry formulation and applied with a washing machine or other application device, the composite particles become entrapped in the weave of the textile due to electrostatic interactions between the typically negatively charged textile fiber surface and the positively charged composites; as well as due to physical entrapment, such as one might see with a coffee filter. Upon drying, the particles typically remain in the textile product for 1-5 launderings or even more. During wear and wash, silver ions are released from the composite structure in the presence of moisture, sweat and/or humidity and redeposited onto the fiber surface in the form of silver particles due to photoreduction of silver chloride salts.

Silver is readily oxidized and reduced in the presence of an external stimulus. In fact, it is the oxidation of silver in the presence of moisture or humidity that allows for the release and migration of silver ions necessary to provide the active biocidal or antibacterial properties of silver. Thus, while the composite structure delivers the silver to the surface of a garment, the silver present in the composite undergoes oxidative and/or reductive transformations over a period of time in the presence of moisture or more importantly perspiration/sweat once the silver is on the garment.

Sweat contains sodium chloride among other chemicals that can react with silver to form byproducts such as silver chloride (a very weakly soluble silver salt). Thus, when the silver ions are released they can react with the Cl− ions and reprecipitate directly on the fiber surface. Since the silver present in the composite additive is exposed (i.e. it is not embedded with the particles) and is at a high localized concentration, it can more readily be released and subsequently reprecipitate. Short to medium term retention (for example, between 3 and 10 launderings) of a disclosed composite additive in textiles is believed to be largely due to entrapment of the particles in textile weave and on a textile fiber surface as a consequence of composite aggregate size, surface charge/zeta potential of the particles, and non-specific bonding (e.g. van der Waals forces) that occurs when the product is dried onto the textile. Longer term retention of silver (for example >10 launderings) on the textile is believe to be due to transformation of the silver once it is on the garment. By way of example, as the sweat is released from the body, moisture in the sweat will solubilize silver ions from the composite which will then reprecipitate elsewhere in the form of silver chloride (which is less soluble than the silver in silver metal). The silver chloride will adhere to the fiber surface once it is dried providing the longer term retention, even though the particle of the composite is no longer in the fabric.

In embodiments, a laundry additive composition is made up of composite particles, the composite particles having a carrier component and an active silver component. In embodiments, the carrier component comprises one or more different inorganic support particles, such as a mixture of particles, wherein at least one of the inorganic support particles is a pigment particle. Functionally speaking, the inorganic support particles provide a chemically-inert, stable support for the active silver component. In addition, they provide the ability to suspend the laundry additive composition in aqueous solutions (either intrinsically or through the use of selected surfactants), and mask color shift associated with the use of silver and/or silver containing compounds. Thus, in embodiments, the inorganic support particles provide a chemically-inert, stable support for the silver component. The materials of the inorganic support particles are typically selected to withstand the chemical and/or thermal processing steps required to produce the composite, and to minimize potential for skin sensitivity and environmental impact. Further, the inorganic support particles may be selected to enhance the adherence or interaction between the additive and the surface of the textile fibers, and to enable the materials to be entrapped in the textiles using a selected application method, such as a wash-in or spray-on an application method.

In embodiments, the inorganic support particles include one or more types of inorganic, ceramic, or mineral particles that serve as a carrier/substrate for metallic silver particles or silver salts that can be incorporated into laundry formulations. In embodiments, the inorganic support particles include ceramic and/or mineral particles such as natural mineral or synthetic ceramic particles that can be dispersed in water either by themselves or with the aid of dispersant. A wide range of dispersants can be used to improve the aqueous dispersions of pigment and ceramic particles including polymers such as polyacrylic acids, polycarboxylates, polyurethanes, alkoxysilanes (e.g. 3-aminopropyltriethoxysilane), or polyethyleneimine. In certain embodiments, a dispersants comprises a polyacrylic acids and/or alkoxysilanes. In embodiments, the inorganic support particles comprise ceramic particles and/or mineral particles.

The shape of the particles is generally considered to be irregular particulate or granular and selected such that a particle has a solid granulated/powdered appearance that is homogeneous in color and easily suspendable in water. Visual inspection of the powder reveals agglomerates that can be as large as 500 µm. However, these agglomerates break apart when formulating. At the microscopic scale, the individual components (inorganic phase(s) and silver phase) are well-mixed with silver bonded to/deposited on both phases as well as bridging between the inorganic support particles (see, for example, FIGS. 1-9).

Figure 2:
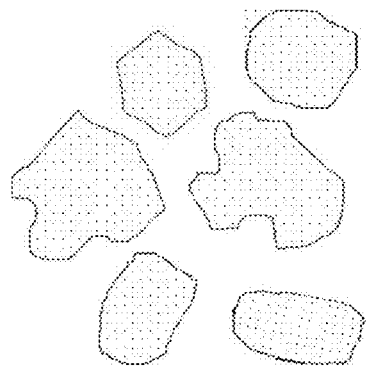
FIG. 2 is a schematic showing white or non-pigment particles with irregular shape and average size between 250-500 nm, in accordance with embodiments disclosed herein.
Figure 3:
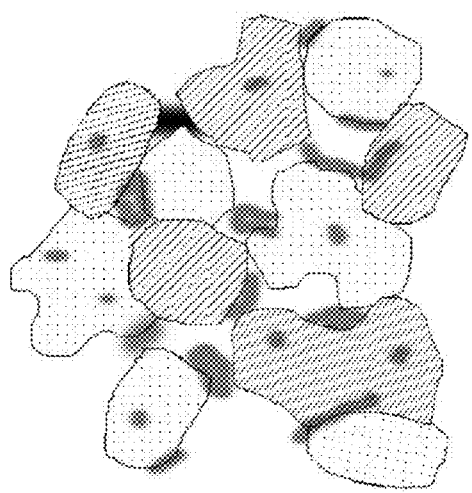
FIG. 3 is a schematic showing blended pigment powder bound together with silver salt on the surface and at the interface of the various particles, in accordance with embodiments disclosed herein. The dark grayish areas represent silver salt.
Figure 4:
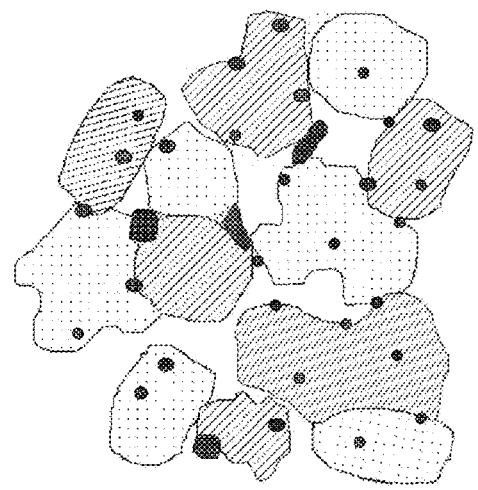
FIG. 4 is a schematic showing blended pigment powder bound together with metallic silver islands plated onto the surface through heat treatment, in accordance with embodiments disclosed herein. The dark sports represent metallic silver deposits.
Figure 5:
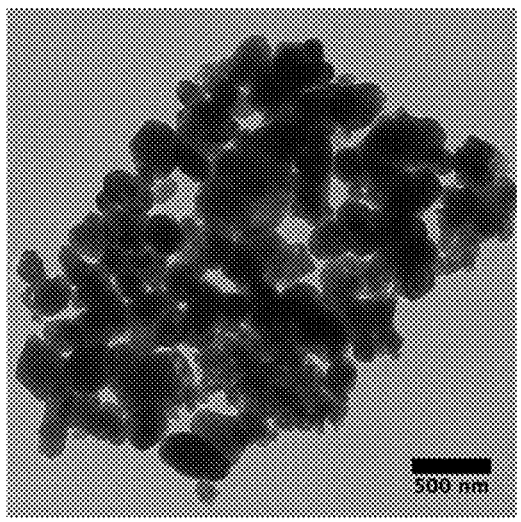
FIG. 5 is a digital image showing a transmission electron microscope (TEM) image of composite laundry additive powder coated with and bound together with silver salt, in accordance with embodiments disclosed herein.
Figure 6:
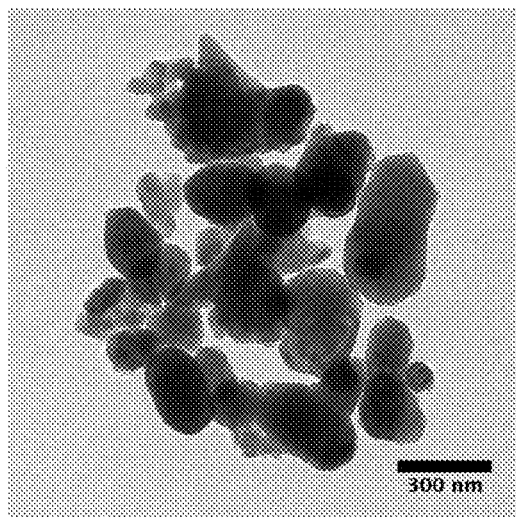
FIG. 6 is a digital image showing a TEM image of composite laundry additive powder coated with and bound together with silver salt, in accordance with embodiments disclosed herein.
Figure 7:
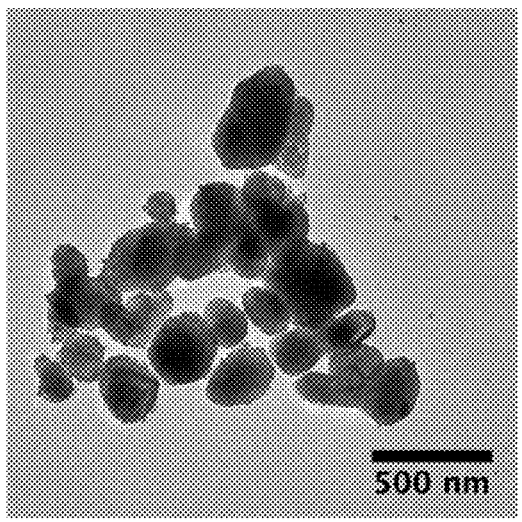
FIG. 7 is a digital image showing a TEM image of composite laundry additive powder coated with and bound together with metallic silver particles, in accordance with embodiments disclosed herein.
Figure 8:
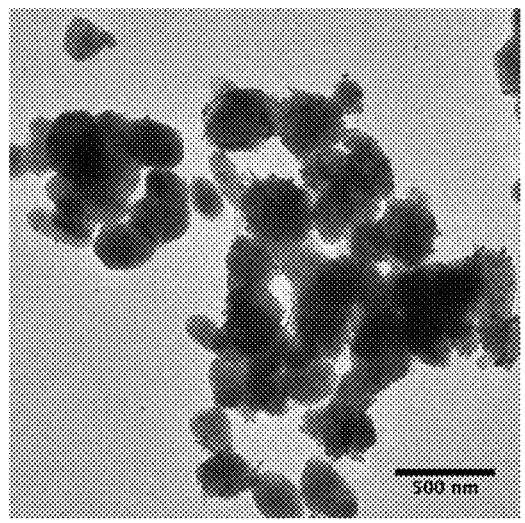
FIG. 8 is a digital image showing a TEM image of composite laundry additive powder coated with and bound together with metallic silver particles, in accordance with embodiments disclosed herein.
Figure 9:
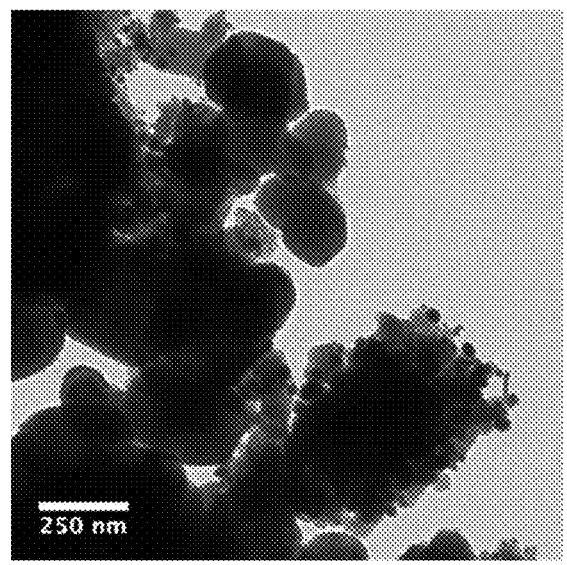
FIG. 9 is a digital image showing a TEM image of composite laundry additive powder coated with and bound together with metallic silver particles, in accordance with embodiments disclosed herein.

FIGS. 1 and 2 are representative of different pigment and non-pigment inorganic particles that have irregular shape and size. The average particle size is between about 0.1 µm and about 1.0 µm, but aggregates and agglomerates can be larger. FIG. 3 shows a schematic of a well-blended mixture of the two pigment/inorganic particle types with silver salt deposited onto the surface of the particles. The silver salt has a poorly defined structure and appears as deposits on the surface of the pigment particles. FIG. 4 shows a schematic of metallic silver particles deposited onto the blended pigments. The metallic silver particles are produced either by chemical or thermal reduction of the metal salt treated composite. FIGS. 5 and 6 are Transmission electron microscope (TEM) digital images of the composite additive with silver salt on the surface of the particles and holding the particles together in agglomerates. As described above, the salt is poorly defined but coating the particles. FIGS. 7-9 show TEM digital images of the composite additive with metallic silver incorporated into the structure. The metallic silver appears as dark circular spots on the surface and at the interface between the pigment/inorganic particles. Silver is not found by itself, but rather integrated into the composite structure.

Figure 10:
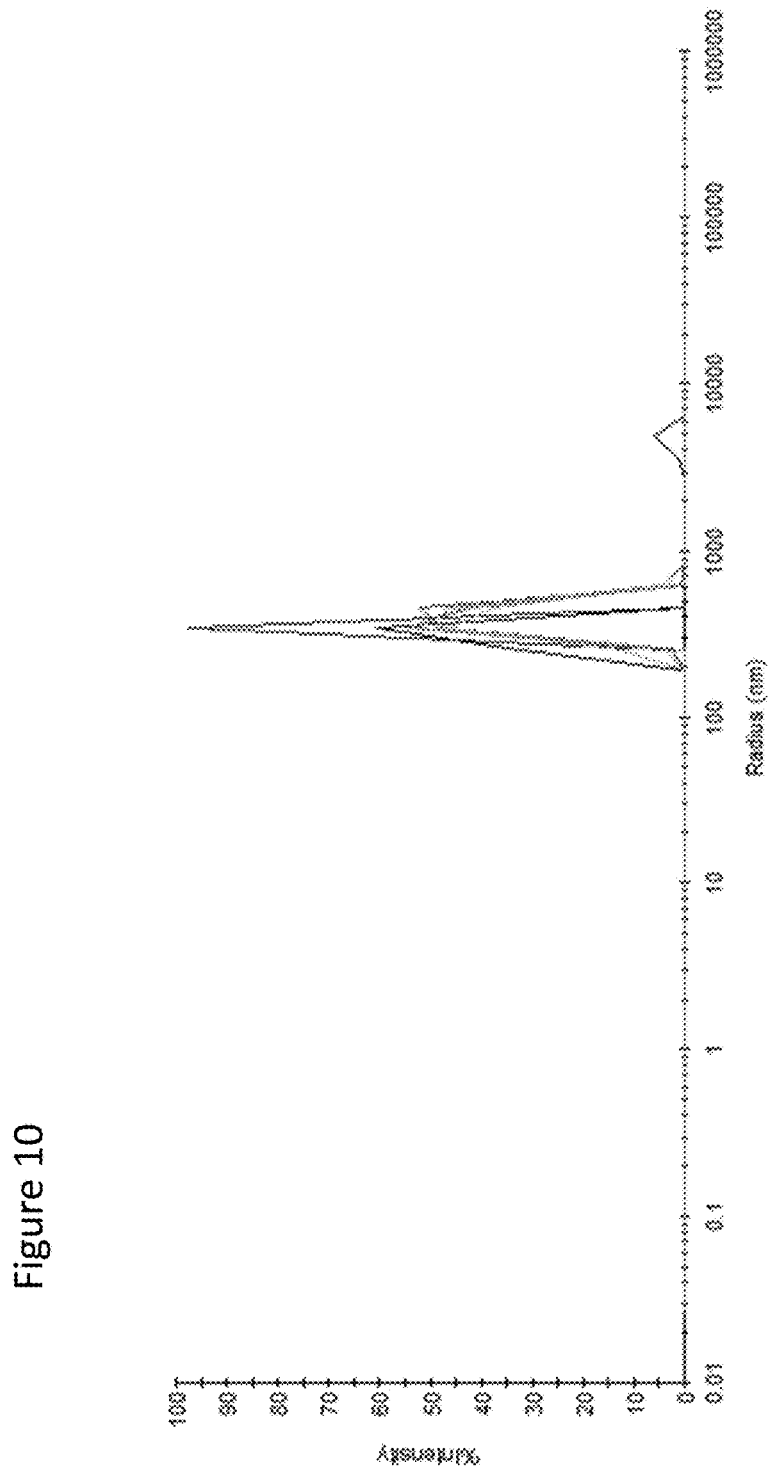
FIG. 10 is a graph showing a dynamic light scattering spectrum of composite laundry additive suspended in water at a working concentration of 25 ppm solids, which corresponds to a silver concentration of approximately 1 ppm silver. The average hydrodynamic radius of these particles suspended in solution is approximately 400 nm.

Particle size influences several aspects of the composite properties. First, the surface area is proportional to the particle size, with smaller particles having a greater surface area per particle volume. The inorganic support particles are fully dense particles and have no significant microporosity. Hence, in order to maximize the available surface for the deposition of silver compounds, a smaller particle size is desirable. Similarly, smaller particles aid in the dispersibility of the compound. On the other hand, particles that are too fine will not become entrapped in the textiles. Given these balancing influences, the optimal average particle size for the inorganic support is in the range of about 0.1 to about 1.0 µm (100-1000 nm), with preferred sizes in the 200-500 nm range. In certain embodiments, the composite granular/powder size is in the range of about 0.5 µm to about 20 µm (which may include multiple pigment particles and the silver additive), with the average hydrodynamic diameter when suspended in water of about 0.5 µm to about 1.0 µm (see, for example FIG. 10). In practice, the material is ideally comprised of not only individual crystallites, but also small agglomerates of these particles, with the agglomerates ranging in size up to about 10 µm or larger for example as large as about 500 µm. For example, when in powder form, there are some larger agglomerates up to 500 µm, but these breakup when dispersed in water to the 0.5-20 µm size. In embodiments, the inorganic support particles are generally an irregular particulate or granular. In embodiments, inorganic support particles have a diameter of a between about 0.1 and about 1.0 µm.

Figure 11:
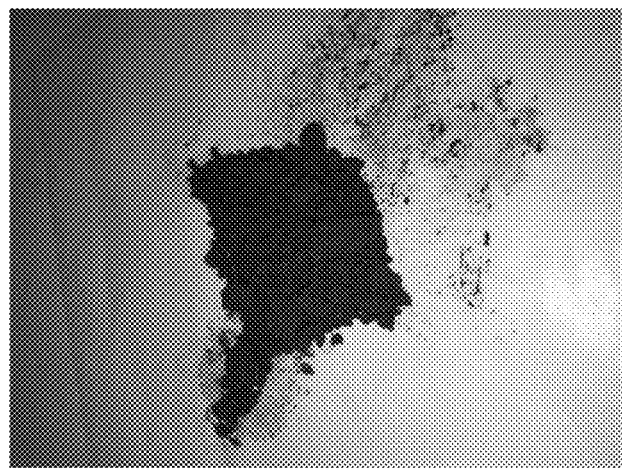
FIG. 11 is a digital image of blue pigment, in accordance with embodiments disclosed herein
Figure 12:
FIG. 12 is a digital image of white pigment, in accordance with embodiments disclosed herein

One of the important features of the disclosed compositions is that the inorganic support particles include pigments, such as mineral pigments, that mask color shift that is often imparted by the silver particles or silver salt and prevent visual darkening that often occurs due to photoreduction of metal salts. As described above, silver particles tend to be yellow or brown while many silver salts photoreduce to form a grayish appearance. Accordingly, articles that are treated with silver or silver salts also look yellowish or gray, which may be unpleasing aesthetically. Thus as disclosed herein, integrated pigmentation with strong tinting strength is used to offset this color shift. The use of mineral or inorganic pigments to alter the appearance of textiles goes back thousands of years. More recently, products, such as bluing agents, have been used to improve the appearance of dingy white clothing. Bluing agents can be described as colloidal solutions of inorganic blue pigments such as Prussian blue or ultramarine blue that can be added during laundry. Bluing agents make fabrics appear whiter because the human eye views slightly blue tints as very white. When properly used, small amounts of residual pigment are retained in the weave of the fabric and add a hint of blue to fabrics, which makes them appear whiter to the eye. The powdered pigments used in the bluing agents have an intense deep blue color with a strong tinting strength. The impact of the deep color can be manipulated by controlling the concentration or by blending with other pigments, (e.g. white pigments, see, for example FIG. 12, to form a light blue color). In particular, the use of blue pigmentation (such as ultramarine blue, see for example, FIG. 11) enhances the perception of whiteness in garments. As disclosed herein, the high tinting strength of the pigments minimizes any impact that silver has on the treated articles. Thus, in embodiments, the disclosed laundry additive compositions include, as a constituent of the inorganic support particles, particles that are pigment particles. In embodiments, the pigment particles have one or more of a blue color, a white color, a red color, a green color, a yellow color, a violet color, a black color, or any combination thereof. For example, the different pigment particles can be combined in a composite laundry additive to create virtually any color. In embodiments, the composite laundry additive is substantially homogeneous in color. In general, pigments are selected to meet the functional requirements from chemistries that are widely available, low cost, generally considered safe and non-toxic. In embodiments, the pigment particle comprises an ultramarine pigment, an aluminosilicate pigment, a titanium oxide pigment, an iron-based pigment, an iron oxide pigment, a copper-based pigment, a silica pigment, or any combination thereof. In embodiments, the copper based pigment comprises a hydrated copper carbonate, a copper silicate, or a combination thereof. In embodiments, the pigment particles in the composite laundry additive comprise a total weight percentage of the composition of between about 90% and about 99.9%, such as between about 90% to about 95%, about 95% to about 99.9%, about 92% to about 97% and the like. The color of the composite additive is influenced primarily by the pigment color, the silver content, and the ratio of colored pigment to white pigment or non-pigment inorganic material diluents. The ratio of the inorganic components within a given formula is typically dictated by the desired color and suspendibility. In a preferred composition, the ratio of blue pigment to white pigment is about 1:3, corresponding to about 25% by weight blue pigment to 75% by weight white pigment. In some embodiments, the blue pigment varies from 15% blue to about 50% blue, by weight with the remainder being other pigment or non-pigment inorganic materials, for example from about 15% to about 25%, about 20% to about 30%, about 25% to about 35%, about 30% to about 40%, about 35% to about 45%, about 40% to about 50%, and the like. In general, the desire is to minimally shift the color of treated articles such that they appear the same color as the article would without treatment. In an embodiment, the solid powder composite is light blue in color.

In certain embodiments, a composite laundry additive, employs a blend of ultramarine blue and $TiO_2$ (anatase) white pigments to produce a light blue powder. Ultramarine blue is a complex sulfur-containing sodium aluminosilicate ($Na_{8-10}Al_6Si_6O_{24}S_{2-4}$) mineral that is believed to derive its deep blue color from an $S_3$-radical anion in the crystal structure. While this inorganic pigment is now synthetically produced, it was originally produced by finely grinding the mineral lapis lazuli. When ground to sufficiently small size, the blue powder can be suspended in water due, in part, to its positive zeta potential and hydrophilic surface. This positive zeta potential also enhances its adherence to textiles fibers that often have a negative surface charge. This effect is similar to the way that cationic surfactants are used in fabric softeners to adhere to the fiber surfaces. Ultramarines have also been produced in green, violet, and red colors by varying the sulfur environment and are explicitly included in this invention. The color is permanent unless heated to >400 C or treated with strong hydrochloric acid.

In embodiments, inorganic support particles in a composition have a positive zeta potential and provide some net positive charge on the surface. A positive zeta potential of sufficient magnitude is indicative of the stability of colloidal dispersions. For example the magnitude of the zeta potential indicates the degree of electrostatic repulsion between adjacent, similarly charged particles in dispersion. For molecules and particles that are small enough, a high zeta potential will confer stability, i.e., the solution or dispersion will resist aggregation. In embodiments, the composite particles have a positive zeta potential, such as a zeta potential greater than about 30 mV, for example greater than 40 mV, greater than 40 mv, or even greater than 60 mV. In embodiments, a particle is coated with one or more of $SiO_2$ and $Al_2O_3$ to provide a positive zeta potential with improved water suspendability.

In some embodiments, the inorganic support particles have surface functionality to influence: the ability of the particles to be suspended in aqueous solutions; the compatibility of the ingredients during processing; and the interaction of the resulting composite additive with the textile fibers. An important property related to surface functionality is that the particle surface is hydrophilic and that at least one of the particles has a positive surface charge (or positive zeta potential) for the conditions in which the additive will function. This positive surface charge enhances suspension stability and facilitates attractive interactions between the composite additive and the fiber surface that generally has a negative surface charge. The positive surface charge can be derived from the intrinsic properties of the inorganic component or from surface modifications that alter the surface charge of materials such as $TiO_2$. In embodiments, the composite particles have a net positive charge. In embodiments, the inorganic support particles comprise surface modifications that alter the surface charge. In embodiments, $TiO_2$ is used for the production of a homogeneous suspendable powder that does not result in appreciable color segregation. In particular embodiments, $TiO_2$ pigments with particle size <1 μm are coated with combinations of $SiO_2$ and $Al_2O_3$ to provide a positive zeta potential with improved water suspendability.

In embodiments, the active silver component comprises a silver metal or silver salt deposited onto one or more of the inorganic support particles. The silver metal or salt particles typically are deposited onto the inorganic support particles, for example, as silver nitrate salt, and transformed into either weakly soluble silver salts (such as silver carbonate) and/or reduced to metallic silver particles by chemical and/or thermal reactions. In embodiments, the silver or silver salt comprises metallic silver, silver oxide, silver chloride (AgCl), silver carbonate ($Ag_2CO_3$), silver citrate ($C_6H_8Ag_3O_7$), silver acetate ($AgC_2H_3O_2$), silver stearate ($Ag[CH_3((CH_2)_{16})CO_2]$) silver cyanurate ($Ag_3C_3N_3O_3$), or a combination thereof. The function of the silver in the additive is to provide anti-odor and/or anti-bacterial properties to the surface of the textile. The loading of the silver in the composite powder typically ranges from 1,000 ppm to 100,000 ppm which is defined as mg Ag/kg of composite material. On a wt % basis, this corresponds to about 0.1 wt % to about 10 wt % Ag, with a preferred composition being 4 wt % (or 40,000 ppm). This loading does not include the mass of the counter ions for silver salts. In embodiments, the silver metal or silver salt in the composite laundry additive comprise a total weight percentage of between about 0.1% and about 10% silver, such as about 0.1% to about 9.0%, about 0.3% to about 5.0%, about 0.6% to about 7.0%, about 1.0% to about 4.0%, about 2.4% to about 6.5%, and any in between about 0.1% and about 10%. In embodiments, the silver metal or silver salt serves as a binder for the one or more inorganic carrier particles. Silver metal or silver salts aids in binding the different particles together to prevent segregation of the different components and facilitate the formation of a more homogeneous product. In embodiments, the inorganic support particles mask color shift associated with the use of silver and/or silver containing compounds.

The silver metal and/or salt is incorporated into the composite via a multistep process involving dispersion of silver nitrate on the surface of the solid inorganic phase followed by chemical and thermal transformation of the silver nitrate to the desired silver metal or salt. The size of the silver phase within the composite structure is optimized in the 100-200 nm size range as deposited onto the inorganic phase, but the silver can range from <100 nm to 1 μm. There is little or no "free" silver component, i.e. it is all in close association (i.e. stuck to) the inorganic support. Further, in some examples (see, for example, FIGS. 3-8) it bridges different inorganic support particles to form agglomerates. The shape of the silver phase within the composite includes spheroids, plates, cubes, and the like.

Figure 13:
FIG. 13 is a digital image of a composite laundry additive, in accordance with embodiments disclosed herein.
Figure 14:
FIG. 14 is a digital image of composite laundry additive suspended in water, in accordance with embodiments disclosed herein.

The method for producing the composite additive results in a visually homogeneous pale-blue powdered material that can be "smeared" with little or no streaks (see, for example, FIG. 13). When formulated into a laundry product such as an aqueous colloidal solution, the composite material retains its color homogeneity (see, for example, FIG. 14). Further, when random samples are analyzed for silver content, there appears to be uniform distribution of the silver. This uniformity is derived from the 1) the size and size distributions of the pigment ingredients, 2) a high degree of mixing pigments, such as mixing of $TiO_2$ and ultramarine pigments, 3) the uniform distribution of silver precursor within the mixed pigments, and 4) the subsequent chemical and thermal transformations of the silver precursor to enhance cohesive interaction between the different pigment components.

Disclosed is a kit for reducing and/or inhibiting odor formation or bacterial growth on a garment. In embodiments, the kit includes one or more containers, wherein at least one of the one or more containers comprises the composite laundry additive disclosed herein. In embodiments, the kit further includes directions for using the kit.

Also disclosed is a method of treating a textile to impart antibacterial properties. In embodiments, the method includes contacting the textile with the composite laundry additive disclosed herein in an aqueous environment to disperse the composite laundry additive on and within the textile; and drying the textile. In some embodiments, a "final rinse" step of laundering cycle is used to "wash-in" composite laundry additive (as a component of a laundry product). This uses the same feature of the washing cycle as the softener does. In some embodiments, the textile is contacted in a washing machine. In some embodiments, the textile is contacted by use of a spray bottle.

Also disclosed are method of producing composite material. The method includes thorough mixing of inorganic pigments and other inorganic support, addition of silver nitrate to produce homogeneous distribution of silver; chemical transformation of silver; thermal processing to further transform silver and help bind inorganic support particles and dispersion/formulation.

Example

This example describes a formulation of a wash-in or spray-on laundry product using composite laundry additive.

An aqueous suspension of composite additive powder to be used as an odor reduction product that can be added to the softener compartment of most consumer washing machines for rinse-in during final rinse. The Suspension comprised of 0.5 wt. % to 5 wt. % composite solid (up to 99+% water), with the preferred suspension composition at 1 wt. % solid (corresponds to 400 ppm Ag in solution). In addition to powder, other additives/adjuvants can be added to improve the stability of the suspension.

Aqueous suspension of composite additive powder to be used as an odor reduction product that can be sprayed onto desired area using trigger spray or other spray apparatus. Suspension comprised of 0.01 wt. % to 0.1 wt. % composite solid (up to 99.9+% water), with the preferred suspension composition at 0.05 wt. % solid (corresponds to 400 ppm Ag in solution). In addition to powder, other additives/adjuvants can be added to improve the stability of the suspension.

Blended solid powder of composite additive and laundry detergent that can be used as a stand-alone detergent/deodorizer. In this case, using the preferred composition of the composite additive containing 4 wt % Ag, the laundry detergent blend would contain up to 2.5 wt. % additive.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein.

Therefore, it is manifestly intended that embodiments be limited only by the claims and the equivalents thereof.

We claim:

1. A composite laundry additive, of composite particles, comprising:
   a carrier component comprising one or more different inorganic support particles, wherein at least one of the inorganic support particles is a pigment particle; and
   a silver component comprising a silver metal or silver salt disposed on one or more of the inorganic support particles,
   wherein the silver metal or silver salt in the composite laundry additive comprises a total weight percentage of between about 0.1% and about 10% silver.

2. The composite laundry additive of claim 1, wherein the silver metal or silver salt serves as a binder for the one or more inorganic carrier particles.

3. The composite laundry additive of claim 1, wherein the one or more inorganic support particles comprises a ceramic particle or a mineral particle.

4. The composite laundry additive of claim 1, wherein the pigment particle comprises an ultramarine pigment, an aluminosilicate pigment, a titanium oxide pigment, an iron-based pigment, an iron oxide pigment, a copper-based pigment, a silica pigment, or any combination thereof.

5. The composite laundry additive of claim 4, wherein the copper based pigment comprises a hydrated copper carbonate, a copper silicate, or a combination thereof.

6. The composite laundry additive of claim 1, wherein the pigment particles in the composite laundry additive comprise a total weight percentage of the composition of between about 90% and about 99.9%.

7. The composite laundry additive of claim 1, wherein the silver or silver salt comprises metallic silver, silver oxide, silver chloride (AgCl), silver carbonate ($Ag_2CO_3$), silver citrate ($C_6H_8Ag_3O_7$), silver acetate ($AgC_2H_3O_2$), silver stearate ($Ag[CH_3((CH_2)_{16})CO_2]$), silver cyanurate ($Ag_3C_3N_3O_3$), or a combination thereof.

8. The composite laundry additive of claim 1, wherein the inorganic support particles provide a chemically-inert, stable support for the silver component.

9. The composite laundry additive of claim 1, wherein the inorganic support particles mask color shift associated with the use of silver and/or silver containing compounds.

10. The composite laundry additive of claim 1, wherein pigment particles have one or more of a blue color, a white color, a red color, a green color, a yellow color, a violet color, or a black color.

11. The composite laundry additive of claim 1, wherein the inorganic support particles are an irregular particulate or granular.

12. The composite laundry additive of claim 1, wherein composite laundry additive is homogeneous in color.

13. A kit for reducing and/or inhibiting odor formation or bacterial growth on a garment, comprising:
    one or more containers, wherein at least one of the one or more containers comprises the composite laundry additive of claim 1.

14. The kit of claim 13, further comprising directions for using the kit.

15. A method of treating a textile to impart antibacterial properties, comprising:
    contacting the textile with the composite laundry additive of claim 1 in an aqueous environment to disperse the composite laundry additive on and within the textile; and
    drying the textile.

16. A composite laundry additive, of composite particles, comprising:
    a carrier component comprising one or more different inorganic support particles, wherein at least one of the inorganic support particles is a pigment particle, wherein the inorganic support particles have a diameter of between about 0.1 and about 1.0 µm; and
    a silver component comprising a silver metal or silver salt disposed on one or more of the inorganic support particles.

17. A composite laundry additive, of composite particles, comprising:
    a carrier component comprising one or more different inorganic support particles, wherein at least one of the inorganic support particles is a pigment particle, wherein the inorganic support particles comprises surface modifications that alter the surface charge; and
    a silver component comprising a silver metal or silver salt disposed on one or more of the inorganic support particles.

18. The composite laundry additive of claim 17, wherein the composite particles have a net positive charge.

19. The composite laundry additive of claim 17, wherein the composite particles have a positive zeta potential.

* * * * *